(12) United States Patent  (10) Patent No.: US 8,784,654 B2
Wulfman  (45) Date of Patent: Jul. 22, 2014

(54) METHODS AND SYSTEMS FOR BIOLOGICAL SAMPLE COLLECTION AND ANALYSIS

(75) Inventor: Edward I. Wulfman, Woodinville, WA (US)

(73) Assignee: Bayer Medical Care, Inc., Indianola, PA (US)

( * ) Notice: Subject to any disclaimer, the term of this patent is extended or adjusted under 35 U.S.C. 154(b) by 909 days.

(21) Appl. No.: 12/742,908

(22) PCT Filed: Nov. 14, 2008

(86) PCT No.: PCT/US2008/083695
§ 371 (c)(1),
(2), (4) Date: Sep. 16, 2010

(87) PCT Pub. No.: WO2009/065082
PCT Pub. Date: May 22, 2009

(65) Prior Publication Data
US 2011/0151463 A1    Jun. 23, 2011

Related U.S. Application Data

(60) Provisional application No. 61/003,118, filed on Nov. 14, 2007.

(51) Int. Cl.
*B01D 35/18* (2006.01)
*B01D 37/00* (2006.01)
*A61M 1/36* (2006.01)

(52) U.S. Cl.
USPC .......... 210/185; 210/435; 210/774; 604/5.03; 604/6.09

(58) Field of Classification Search
None
See application file for complete search history.

(56) References Cited

U.S. PATENT DOCUMENTS

| 4,350,156 | A | * | 9/1982 | Malchesky et al. | .......... 604/6.04 |
| 4,634,417 | A | | 1/1987 | Korec | |
| 5,252,221 | A | | 10/1993 | van Dommelen et al. | |
| 5,827,229 | A | | 10/1998 | Auth et al. | |
| 5,938,645 | A | | 8/1999 | Gordon | |
| 6,106,483 | A | * | 8/2000 | Guirguis | ........................ 600/562 |
| 6,497,675 | B1 | | 12/2002 | Davankov | |
| 6,565,588 | B1 | | 5/2003 | Clement et al. | |
| 6,746,600 | B2 | * | 6/2004 | Nguyen | .................. 210/167.06 |
| 6,749,747 | B1 | * | 6/2004 | Olapinski et al. | ............. 210/184 |
| 6,818,001 | B2 | | 11/2004 | Wulfman et al. | |
| 7,316,779 | B2 | * | 1/2008 | Pressman et al. | .......... 210/416.1 |
| 7,344,546 | B2 | | 3/2008 | Wulfman et al. | |

(Continued)

OTHER PUBLICATIONS

Pathway Medical Technologies, "International Preliminary Report on Patentability," International Bureau of WIPO, International Patent Application No. PCT/US2008/083695, filed Nov. 14, 2008, 6 pages (May 18, 2010).

*Primary Examiner* — Samuel Woolwine
(74) *Attorney, Agent, or Firm* — Ann W. Speckman; Speckman Law Group PLLC

(57) ABSTRACT

Filtration devices for collection and filtration of biological samples are disclosed. Devices having a filtration element oriented in a generally vertical orientation are provided, as well as filtration devices that incorporate a cooling mechanism to reduce the temperature of collected solids. Tissue collection devices, such as aspiration assemblies, tissue sampling devices, and the like incorporating filtration devices are disclosed. Methods of collecting biological samples and separating biological solids from a liquid/solids mixture are also disclosed, together with analytical techniques and protocols for analyzing biological samples.

21 Claims, 4 Drawing Sheets

(56) References Cited

U.S. PATENT DOCUMENTS

| | | |
|---|---|---|
| 2003/0120295 A1 | 6/2003 | Simpson et al. |
| 2003/0125757 A1 | 7/2003 | Patel et al. |
| 2004/0019310 A1 | 1/2004 | Hogendijk |
| 2004/0079089 A1* | 4/2004 | Wallach .......................... 62/3.2 |
| 2004/0127854 A1* | 7/2004 | Leinsing et al. ......... 604/167.03 |
| 2004/0167467 A1 | 8/2004 | Harrison et al. |
| 2005/0154407 A1 | 7/2005 | Simpson |
| 2005/0177068 A1 | 8/2005 | Simpson |
| 2005/0222663 A1 | 10/2005 | Simpson et al. |
| 2006/0032508 A1 | 2/2006 | Simpson |
| 2006/0141497 A1 | 6/2006 | Finkelstein et al. |
| 2006/0235366 A1 | 10/2006 | Simpson |
| 2006/0236019 A1 | 10/2006 | Soito et al. |
| 2006/0270974 A1 | 11/2006 | Goff et al. |
| 2007/0038173 A1 | 2/2007 | Simpson |
| 2007/0078469 A1 | 4/2007 | Soito et al. |
| 2010/0203562 A1* | 8/2010 | Binder et al. ................... 435/13 |

* cited by examiner

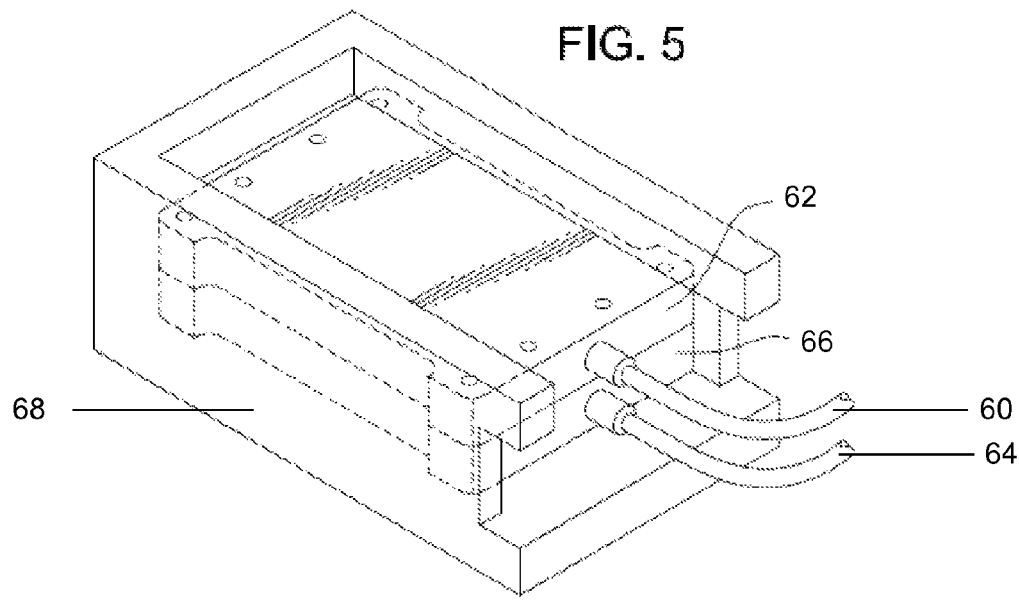
FIG. 5
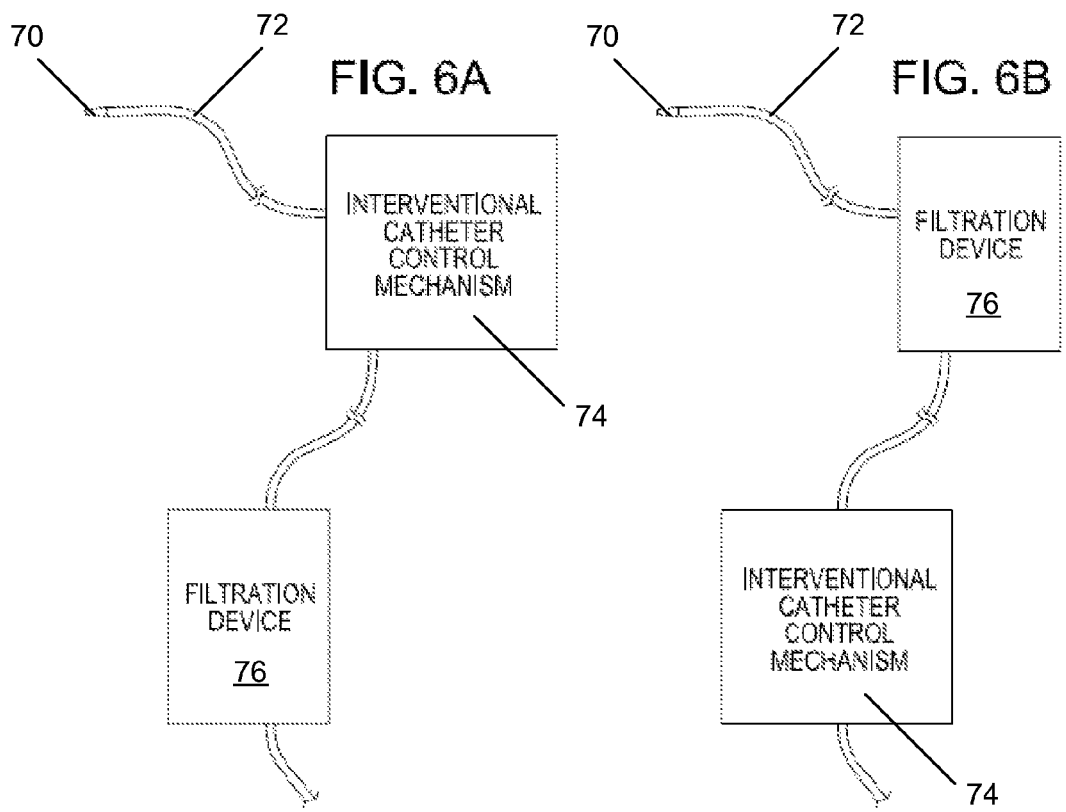
FIG. 6A
FIG. 6B

METHODS AND SYSTEMS FOR BIOLOGICAL SAMPLE COLLECTION AND ANALYSIS

FIELD OF THE INVENTION

The present invention relates, generally, to the collection of biological samples and the preparation of biological samples for analysis. In one aspect, the present invention relates to methods and devices for filtration of biological samples.

BACKGROUND OF THE INVENTION

In general, biological sample collection and analysis techniques are well known. Clinical patient samples are commonly collected for morphological, chemical, cellular and/or molecular analyses. Diagnostic analyses may be performed on whole blood and whole tissue samples, or such samples may be processed to separate the fractions or components of interest prior to analysis. Sample analysis is also performed to analyze the safety and efficacy of therapeutic treatments, and to monitor a patient's condition during ongoing treatment. Access to well characterized patient samples is essential for research and for development of new diagnostic and therapeutic agents and techniques.

Peripheral blood samples are used for many diagnostic purposes and are generally easier and less intrusive to collect than whole tissue samples. The paradigm for biomarker detection in peripheral blood for the detection of various conditions is based on the assumption that important biological factors within tissue enter the blood and can be detected peripherally. Peripheral blood contains low levels of many cellular and molecular markers, however, and detection of many markers using blood samples is difficult due to the low level of markers present in peripheral blood circulation.

Various types of biological tissue samples are therefore sampled, or biopsied, for research and diagnosis, and many types of tissue sampling and biopsy devices are available. Needle-type biopsy devices and endoscopic biopsy devices are well known, for example. Tissue is also collected during invasive or minimally invasive procedures, such as collection of plaque from blood vessels during an atherectomy or plaque excision procedure, for later analysis. Tissue samples generally provide a more probative biological sample than peripheral blood samples, but they also require specialized handling techniques.

Plaque from patients suffering from cardiovascular or peripheral vascular disease may be collected as a strand or as particles carried in a liquid, such as aspirate removed from the site of an intervention. Plaque collection techniques using a plaque excision device that collects plaque as a strand are described, for example, in U.S. Patent Publications 2003/0120295A1; 2003/0125757A1; 2005/0222519A1; 2005/0177068 A1; and 2005/0222663 A1.

Aspirating atherectomy and thrombectomy devices that remove and withdraw plaque and disease tissue from blood vessels are also well known. Filtration devices for use in filtering aspirate collected during a plaque removal procedure have been described, for example, in U.S. Pat. Nos. 5,938,645 and 5,827,229, and in U.S. Patent Publication No. 2006/0270974 A1. One of the challenges in filtering aspirate collected in real time during an interventional procedure is clogging of the filter, which disrupts aspirate collection and may consequently delay or disrupt the interventional procedure. Multiple filter assemblies and/or unfiltered by-pass flow paths have been proposed to avoid interruption of the procedure. The present invention, in one aspect, is directed to providing effective real-time aspirate filtration while avoiding clogging of filtration elements that may interrupt or delay the procedure.

Biological materials are generally sensitive to degradation when exposed to conditions that are different from in situ conditions. Many tissue components decompose and denature, for example, upon exposure to ambient temperatures and conditions following removal from the body. For this reason, biological samples are often chilled or frozen soon after removal from a subject, and some sample preparation techniques, such as centrifugation, are carried out under low temperature conditions. In some cases, entire experimental protocols are carried out in a cold room to prevent degradation of biological materials. Sample collection techniques such as filtration techniques, however, do not generally involve a cooling process unless the filtration is carried out in a cold room. The present invention, in another aspect, is directed to preventing degradation of biological samples during a filtration process.

SUMMARY

In one aspect, methods and systems are provided for treating biological samples comprising both liquid and solid materials to separate at least a portion of the solid materials from liquids by filtration. Biological samples comprising a liquid/solids mixture may be removed from a target site in a subject, such as by aspiration. Fluid and entrained solid and particulate materials may be aspirated from body cavities, lumens, or the like, including blood vessels, cysts, pseudocysts, abscesses, blood vessel grafts, lung passages, bile ducts, ureters, urethras, fallopian tubes, ear canals, joint capsules, the gastrointestinal tract, and the like. Alternatively, biological samples may be removed from a target site in a subject as a substantially solid sample and mixed with a liquid, or otherwise treated to form a liquid/solids mixture, prior to treatment using a filtration device of the present invention. While plaque samples collected from blood vessels are disclosed as specific examples of biological samples collected using filtration devices disclosed herein, it will be apparent that the biological sample may comprise any type of tissue sample, and that filtration devices of the present invention may facilitate collection and preservation of numerous types of tissue samples.

Filtration devices of the present invention may be provided as stand alone devices having an input port for communication with a liquid/solids source material and an output port for withdrawal of liquids from the filtration device. Alternatively, filtration devices of the present invention may be integrated with other devices, such as aspirating catheter assemblies, tissue sampling and/or removal devices, and the like. In general, aspiration is performed by introducing an aspirating catheter or cannula or another structure into a body cavity, lumen or the like, and then removing a tissue sample comprising a liquid/solids mixture by means of suction. Other types of tissue sampling devices may use cutting or coring devices, or other systems for sample removal. Solid or semi-solid tissue samples may be mixed with fluids in connection with the tissue sampling device or in subsequent processing steps. Liquids may be introduced as infusates or irrigants during aspiration and, in that event, may mix with body fluids at the collection site, such as blood, lymph or other bodily fluids, or may be used in connection with solid and semi-solid tissue samples. Suitable biocompatible and sterile infusates and irrigants may comprise liquids such as saline, lactated ringers and other aqueous solutions, and may additionally comprise other agents such as thrombolytic materials, antibiotics, drugs, diagnostic agents, and the like.

In one embodiment, a filtration device may be incorporated in line in an aspiration assembly of the present invention. In one embodiment, for example, a filtration device may be placed between an aspirating or tissue sampling instrument, such as the working head or distal port of an aspirating catheter assembly, and a sample collection device. Where vacuum is used for aspiration from a target site in a body, the filtration device may be positioned in-line with the vacuum source and the aspirating catheter assembly. In another embodiment, a filtration device may be used to filter a liquid/solids mixture withdrawn using an aspiration or another tissue sampling assembly, and the filtration device may operate using a separate vacuum system.

In one aspect, methods and systems of the present invention utilize a filtration device incorporating a generally vertically arranged filtration member. A generally vertical orientation is one in which the plane of the filtration member has a substantial vector component in the direction of gravitational forces. In systems in which the filtration device is incorporated in-line in an aspiration or tissue sampling device, one or more filtration member(s) are provided at a location within the system providing a generally vertical orientation of the filtration member during use of the system. This may be accomplished by the configuration of inlet and outlet ports and chambers, by the positioning of the filtration device during use, or the like.

Orientation of the filtration member in a generally vertical orientation reduces clogging of the filtration member during collection, since the solids tend to collect toward the bottom of the filtration member, while an upper portion of the filtration member remains unclogged, permitting continued liquid flow through the filtration member. Reductions in clogging of the filtration member are especially important when filtration takes place in real-time during a procedure in which tissue is removed from a patient and collected for analysis.

In one embodiment, a filtration device of the present invention comprises a liquid/solids input chamber, a liquid output chamber, and a filtration member interposed between the chambers. The liquid/solids input chamber and liquid output chambers may be enlarged compared to a conduit carrying a liquid/solids mixture, and preferably have suitable intake and output ports that may be connected with suitable conduits for introduction of a liquid/solids mixture and for withdrawal of a substantially liquid output flow.

In another aspect, the present invention relates to a filtration device that provides a cooled environment and reduces the temperature of the liquid/solids mixture input, the solid filtrate, and/or the liquid output. The filtration device may be actively cooled, for example, by contact with a cooling jacket or cooling solids or fluids, or one or more components of the filtration device may incorporate an active cooling element. An active cooling element may be incorporated in one or more structural elements of a collection and/or solute chamber. An active cooling element may additionally or alternatively be provided in a filtration member. Thermoelectric cooling elements are exemplary active cooling elements and are disclosed for use in filtration devices and methods disclosed herein. The temperature of the liquid/solids input mixture, and/or the solid filtrate and/or the liquid output is generally reduced, in or by contact with the filtration device, to a temperature at least 20° F. lower than the temperature of the liquid/solids mixture prior to introduction to the filtration system.

In another aspect, a liquid/solids mixture withdrawn from a target site in a subject may be cooled prior to filtration. In this embodiment, a liquid/solids mixture may be actively or passively cooled during passage through a catheter or conduit or cooled reservoir prior to filtration. Cooling a biological sample prior to filtration may assist in preventing degradation of the sample prior to filtration and may reduce the cooling requirements for filtration.

In yet another aspect, the present invention relates to methods of collecting and analyzing a biological sample using filtration devices of the present invention. The biological sample, as collected, typically comprises a liquid/solids mixture, such as an aspirate, in which solids are entrained, suspended in or carried by a liquid stream. The biological sample may, for example, comprise vascular plaque. Vascular plaque is a complex tissue comprised of several cell types, including endothelial cells, smooth muscle cells, macrophages, lymphocytes and fibroblasts. The quantity of each cell type depends on the type and severity of the plaque. Each cell type produces and responds to numerous factors. Some of these factors promote plaque stability while others promote plaque instability and the resultant serious sequelae of plaque rupture and thrombus formation. In general, it is these factors which are believed to be important as biomarkers of disease.

Plaque analysis is an important and sensitive tool for diagnosis and prognosis, as well as for the early detection of beneficial adaptations in vascular disease, and for the evaluation of potentially efficacious therapies. Since the plaque itself is the origin of most blood biomarkers, detection in the plaque may be performed in the absence of any dilution as is seen in the peripheral blood. The general benefits of plaque analysis include: 1) no dilution of biomarkers in blood; 2) characterization of the site of activity for any therapeutic intervention; 3) increased sensitivity of detection; 4) identification of novel targets for drug development; 5) detection of changes at the earliest time point possible; and 6) a reduction in the number of subjects/patients required to evaluate a treatment or detect a therapeutic effect, with a consequent reduction in the overall cost of therapeutic trials and of drug development. The following table cites vascular plaque biomarkers that have been linked to cardiovascular outcomes, and was adapted from Vulnerable Plaques: A Brief Review of the Concept and Proposed Approaches to Diagnosis and Treatment. AHRQ, Technology Assessment Program, Jan. 22, 2004.

TABLE 1

| Marker | Studies Have Been Conducted on Population Without Known CAD | Laboratory Method | Clinical Outcome Predicted |
| --- | --- | --- | --- |
| C-Reactive Protein (hs-CRP) | Yes | Latex-particle enhanced immunoassay | MI, RV, stroke, death |
| Matrix Metalloproteinase9 (MMP-9) | No | ELISA | Death |
| Soluble Intercellular Adhesion Molecule-1 (sICAM-1) | Yes | ELISA | MI, stroke, death |

TABLE 1-continued

| Marker | Studies Have Been Conducted on Population Without Known CAD | Laboratory Method | Clinical Outcome Predicted |
|---|---|---|---|
| Soluble Vascular Cellular Adhesion Molecule-1 (sVCAM-1) | No | ELISA | MI, stroke, death |
| Soluble E-selection (sE-selection) | Yes | ELISA | MI, stroke, death |
| Interleukin-6 (IL-5) | Yes | ELISA | MI, death |
| Interleukin-18 (IL-18) | No | ELISA | MI, death |
| Tumor Necrosis Factor-alpha (TNF-alpha) | No | cantitative enzyme immunoassay | MI, death |
| Soluble CD40L (immunomodulator) | Yes | ELISA | MI, stroke, death |

Vascular plaque may be removed from a disease site in a subject using any of a variety of plaque excision or material removal devices. Removal of vascular plaque using an aspirating, rotational atherectomy device or another type of aspirating atherectomy or thrombectomy device is preferred for many applications. Aspirating, rotational atherectomy devices such as those described in U.S. Pat. Nos. 6,565,588, 6,818,001 and 7,344,546, which are incorporated herein by reference in their entireties, are suitable for use in methods of the present invention. Filtration methods and devices disclosed herein may be incorporated in such atherectomy and thrombectomy devices, and biological samples may be collected, filtered and preserved in real-time using the disclosed methods and devices.

In yet another aspect, methods and devices of the present invention relate to disease diagnosis and prognosis, and to analyzing biological samples for the presence of various markers that may be indicative of disease state and progression, response to a treatment or test agent, and the like. Screening for drug efficacy or evaluating treatment agents and regimen may be accomplished using techniques described, for example, in U.S. Patent Publications 2005/0154407 A1; 2006/0032508 A1; 2006/0236019 A1; 2006/0235366 A1; 2007/0078469 A1; and 2007/0038173 A1, the disclosures of which are incorporated herein by reference in their entireties. Biomarkers that may be assayed are also disclosed in U.S. Patent Publications 2007/0078469 A1 and 2007/0038173A1, the disclosures of which are incorporated herein by reference in their entireties.

BRIEF DESCRIPTION OF THE DRAWINGS

FIG. 5 illustrates a schematic diagram of a filtration device of the present invention mounted in a jacket.

FIG. 6A shows a schematic diagram illustrating one embodiment of an interventional catheter of the present invention incorporating a filtration device.

FIG. 6B shows another schematic diagram illustrating another embodiment of an interventional catheter of the present invention incorporating a filtration device.

DETAILED DESCRIPTION

In general, a biological sample comprising a liquid/solids mixture is introduced into a filtration device having an inlet port communicating with a first chamber, a filtration member interfacing with the first chamber and with a second chamber, and an outlet port for discharging substantially liquid materials from the second chamber. In operation, the biological liquid/solids mixture is introduced to the first chamber through the inlet port, at least a fraction of the solids are prevented from passing through the filtration member, and liquid passing through the filtration member is withdrawn through the outlet port. The discharge liquid may contain entrained solids having a particle size that passes through the filtration member. Filtration devices of the present invention may comprise multiple filtration members, and additional chamber(s). Where the filtration device comprises multiple chambers, at least one input port is generally provided in a sample collection chamber for communication with a liquid/solids mixture input conduit, and at least one filtrate output port is generally provided in the liquid removal chamber for removal of liquid effluent from the filtration device.

Figure 1:
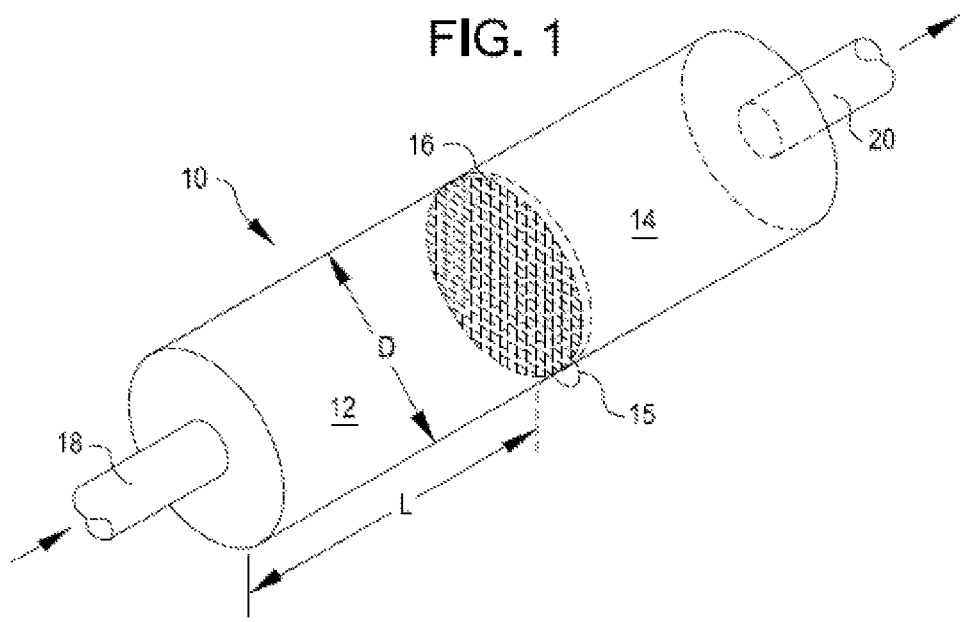
FIG. 1 shows a schematic diagram illustrating a perspective view of a filtration device of the present invention having a generally non-horizontally oriented filtration member.

FIG. 1 schematically illustrates an exemplary filtration device 10 of the present invention comprising a liquid/solids input chamber 12, a liquid output chamber 14, and a filtration member 16 intermediate the input and output chambers. Filtration member 16 may be provided as a fixed, non-removable component of the filtration device, or it may be provided as a removable member and, in this embodiment, may have a tab 15 that projects outwardly from the filters to facilitate placement and withdrawal from the filtration member. Appropriate seals between the filtration member and the input and output chambers may be provided to maintain a substantially sealed system during operation.

Input and output chambers may be provided as discrete chambers having defined internal volumes, as illustrated in FIG. 1. In another embodiment, liquid/solids input chamber 12 may be provided as a portion of a conduit through which a liquid/solids mixture is conveyed from a biological sample collection or operation site in a patient, or as a portion of a conduit communicating with a reservoir containing a liquid/solids mixture. Similarly, liquid output chamber 14 may be provided as a portion of a conduit rather than as a discrete chamber having a defined internal volume.

In embodiments in which input and output chambers 12, 14, respectively, are provided as discrete chambers, a liquid/solids mixture input port 18 communicates with input chamber 12, and a liquid output port 20 communicates with output chamber 14. The input and output ports are generally configured to mate with input and output conduits or other biological sample source and liquid discharge devices. The filtration device and its input and output conduits are generally sealed during sample collection and filtration so that a vacuum or pressure differential may be applied to the filtration device to draw the liquid/solids mixture through the input chamber and across the filtration member, and to discharge liquid effluent from the output chamber through the output port.

Housings forming the sample collection and liquid removal chambers may be generally cylindrical, rectangular, or another configuration. The sample collection and liquid removal chambers may have generally the same configuration and volume, or they may have different configurations and/or volumes. In the embodiment illustrated schematically in FIG. 1, in which the input and output chambers are generally cylindrical and are substantially the same size, the length to diameter (aspect) ratio of the input and output chambers may be approximately 1:1; alternatively the aspect ratio may be greater than 1:1 and up to about 10:1; in yet additional embodiments, the aspect ratio may be less than 1:1 and down to about 1:10.

In one embodiment, the input and output ports are substantially the same configuration and may have a generally cylindrical configuration for mounting input and output conduits, such as tubing. The input and output ports may be provided in generally the same location with respect to the peripheral walls of the associated input and output chambers or they may be provided in different locations on peripheral walls of the associated input and output chambers.

The filtration device illustrated in FIG. 1 is preferably oriented such that the filtration member is oriented in a generally vertical orientation during use. This may be accomplished by positioning the filtration device within an assembly, such as an aspiration catheter assembly, such that during use of the aspirating catheter, the filtration member is arranged in a generally vertical orientation. This may alternatively be accomplished by mounting a filtration device on a support structure or within a larger assembly such that during use, the filtration member is oriented in a generally vertical orientation. This may also be accomplished by providing a support structure on the filtration device itself for supporting the filtration device, during operation, such that the filtration member is oriented in a generally vertical orientation.

Figure 2A:
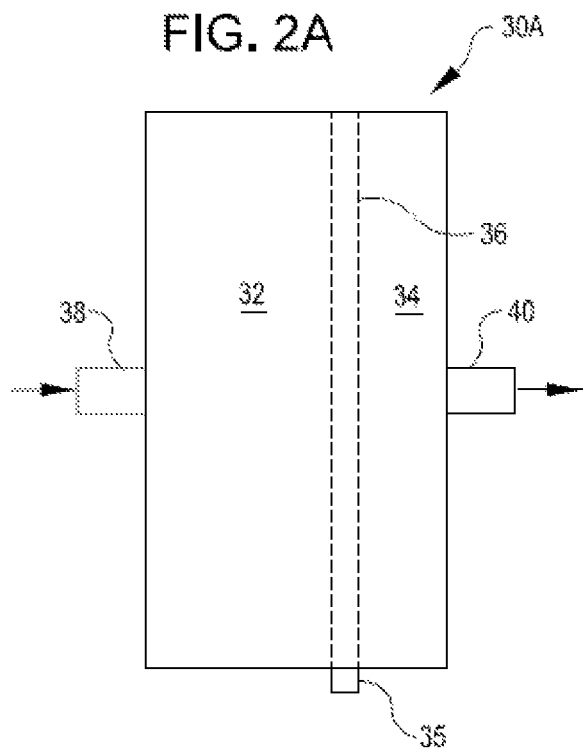
FIG. 2A shows a schematic diagram illustrating a side view of another filtration device of the present invention having a generally vertically oriented filtration member.

In another embodiment, illustrated schematically in FIG. 2A, an exemplary filtration device 30A of the present invention comprises a generally rectangular liquid/solids input chamber 32, a liquid output chamber 34, and a filtration member 36 positioned intermediate the input and output chambers. Filtration member 36 may optionally be provided with a tab or handle 35 that extends from the device to facilitate insertion and withdrawal of the filtration member. A liquid/solids mixture input port 38 communicates with input chamber 32, and a liquid output port 40 communicates with output chamber 34. In the embodiment illustrated in FIG. 2A, the input and output chambers have different sizes, with the input chamber having a larger volume than the output chamber. In this embodiment, the volume of the input chamber may be at least about 110% the volume of the output chamber; in some embodiments at least about 150% the volume of the output chamber; and, in yet other embodiments at least about 200% the volume of the output chamber. Input and output ports 38, 40, respectively, may be arranged in substantially similar locations on peripheral walls of the associated input and output chambers. In alternative embodiment, input and output ports may be arranged in different locations on peripheral walls of the associated input and output chambers.

Figure 2B:
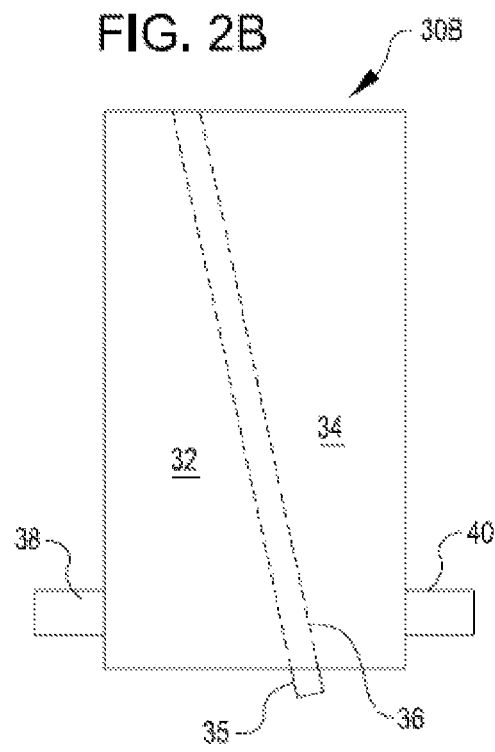
FIG. 2B shows a schematic diagram illustrating a side view of another filtration device of the present invention having a generally vertically oriented filtration member.

FIG. 2B illustrates another embodiment of filtration device 30B in which the filtration member 36 is oriented in a generally vertical orientation in which it is aligned at an angle with respect to gravitational forces. In general, filtration devices of the present invention may employ filtration members oriented at an angle of less than 90° (in either direction from vertical) with respect to gravitational forces. In some embodiments, filtration members may be oriented at an angle, in either direction from vertical, of less than 75° from vertical, less than 60° from vertical or less than 45° from vertical.

Figure 2C:
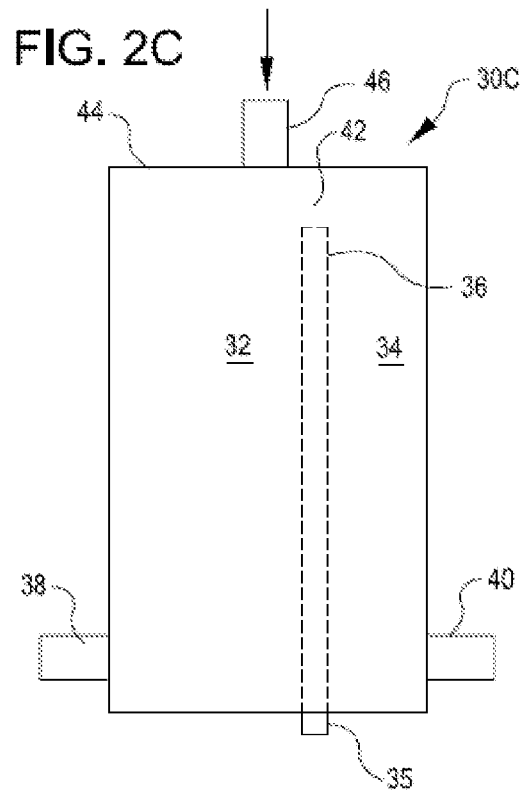
FIG. 2C shows a schematic diagram illustrating a side view of another filtration device of the present invention having a generally vertically oriented filtration member.

In the embodiment illustrated in FIG. 2C, liquid/solids mixture input port 38 and liquid output port 40 are provided in proximity to the bottom surfaces of liquid/solids input chamber 32 and a liquid output chamber 34, respectively. This has the advantage that particles initially collect on a lower region of the filtration member 36, facilitating removal of the particles from the filtration member following collection and reducing the incidence of complete clogging of the filtration member. Also in this embodiment, filtration member 36 is arranged in a substantially vertical orientation, but it does not extend to the top of chambers 32 and 34, leaving a gap 42 between the top of filtration member 36 and the upper surface 44 of filtration device 30C. Gap 42 provides continued flow through the filtration device, even when filtration element 36 becomes partially or fully clogged, allowing fluid flow between liquid/solids input chamber 32 and liquid output chamber 34. In one embodiment, the filtration member may extend at least 65% of the distance between the top and bottom of chambers 32 and 34; in alternative examples, the filtration element may extend at least 70% or at least 75% or at least 80% or at least 85% or at least 90% or at least 95% of the distance between the top and bottom of chambers 32 and 34.

In additional alternative embodiments, the filtration member may extend the full length of chambers 32 and 34, but a portion of the filtration member may have a larger pore size opening, allowing flow of liquids and most solids and thereby rendering clogging of the filtration member.

As illustrated in FIG. 2C, liquid/solids input chamber 32 may also be provided with an additional inlet port 46 through which a fluid, such as deionized water, may be introduced, either continuously or intermittently. Fluid may be provided, for example, to assist in cooling collected filtrate, and/or to rinse collected particles of saline, blood, and other components. The introduced fluid, which may be chilled, may contain agents that aid in the collection and preservation of collected filtrate. Examples of such agents include heparin and other clot-preventing drugs. Different fluids may be introduced at different times during sample collection and filtration.

In one embodiment, the filtration member provides size exclusion filtration and has a pore size that excludes, or traps, particles having a dimension larger than the pore size. Various types of porous materials, such as screens, filters, filtration substrates such as paper, polymers, woven and non-woven membranes, and the like may be provided as filtration members for collection and separation of solids having a threshold size. Suitable filtration members may have a pore size in the range of from about 1 micron to about 1 mm, for example, or from about 5 microns to about 500 microns, such as 40 microns or 70 microns, etc. The pore size may be uniform throughout the surface area of the filtration member, or different pore sizes may be provided at different areas of the filtration device. In one embodiment, for example, the filtration member may have a generally larger pore size in a lower region than at other regions. Multiple filtration members having different pore sizes may be arranged in-line. The filtration member may be coated, or otherwise associated, with a chemical or biological material, or other material that promotes or inhibits a reaction or promotes collection of a particular cellular or molecular species. Suitable coatings and materials are well known in the art. For example, the filtration member may be coated with heparin to minimize the formation of blood clots.

In alternative embodiments, filtration members providing separation of solids on a basis other than size exclusion may be used. Filtration members comprising substrates, such as membranes, beads, and the like, that provide separation of particles based on charge, affinity, or other properties may be used in filtration devices of the present invention.

In another aspect filtration devices having active or passively cooled components are provided to preserve biological samples prior to, during or subsequent to filtration. In one embodiment, solids are cooled at least 20° F., in some embodiments at least 30° F., in some embodiments at least 40° F., and in some embodiments at least 50° F. during their filtration and residence time in the filtration device. The degree of cooling depends on the capacity of the cooling device, the nature and/or size and/or initial temperature of the solids and the liquid/solids mixture, the surface area of solids exposed to the cooler or to cool gases or liquids in a collection and/or withdrawal chamber, the residence time of the solids in the cooled filtration device, and the like. Freezing of solid filtrates may be provided under certain circumstances. Cooling of solid particles to temperatures less than those of the initial sample but above freezing temperatures is preferred for many filtering applications and subsequent analytical procedures.

In one embodiment, cooling of collected solid filtrate is provided by providing a thermoelectric cooling device or surface in association with the filtration device. Thermoelectric cooling systems incorporate two materials having dissimilar properties, such as two dissimilar metals that, upon application of a voltage or current across the dissimilar metal interface, produce a temperature change in the metals. There is generally a cool side and a hot side associated with thermoelectric cooling systems and thermoelectric cooling devices or materials, when used in association with filtration devices of the present invention, are arranged so that the cooling surface is positioned in proximity to the filtration member and the collected solids.

Figure 3A:
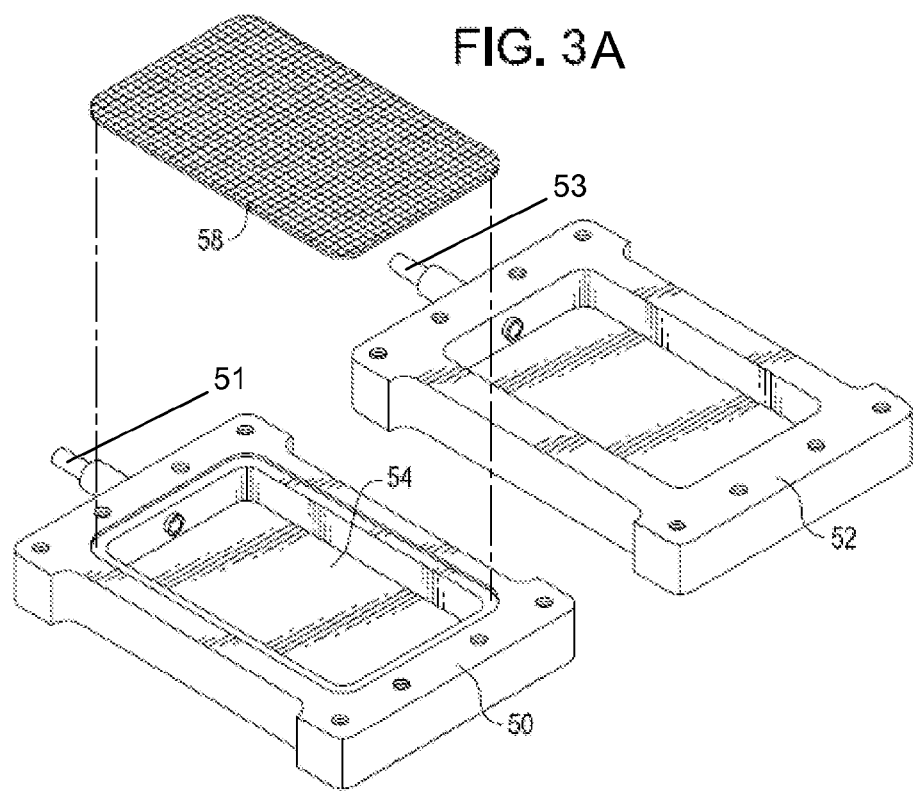
FIG. 3A shows a schematic diagram of components comprising an exemplary cooled filtration device of the present invention, including two mating chambers and a filtration member.
Figure 3B:
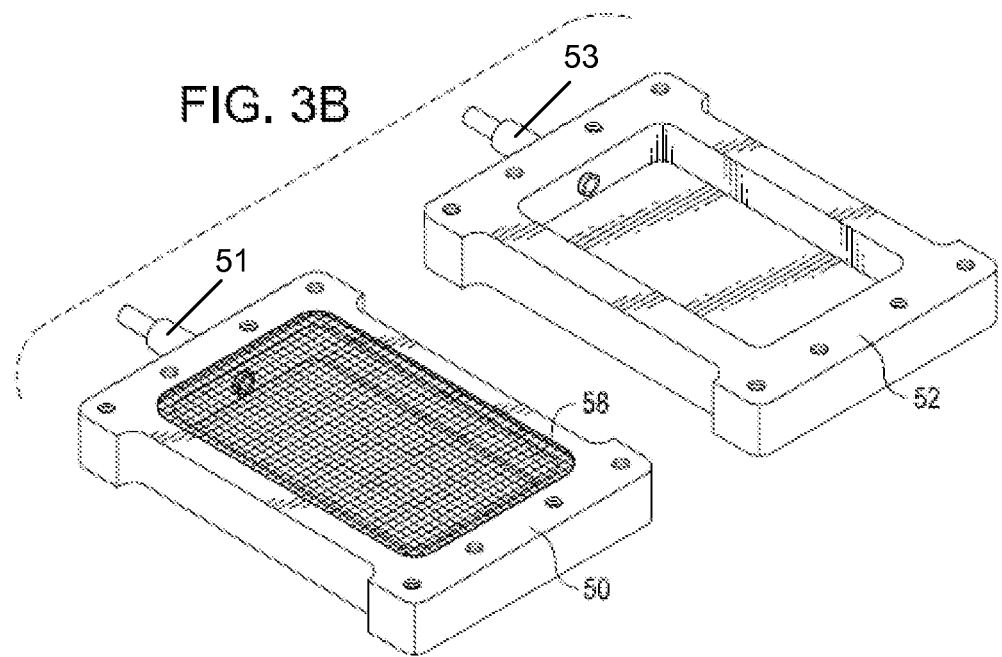
FIG. 3B shows a schematic diagram of components comprising an exemplary cooled filtration device of the present invention with the filtration chamber mounted on an input chamber.

An exemplary prototype device is shown schematically in FIGS. 3A and 3B, comprising an input shell 50 communicating with liquid/solids input port 51, an output shell 52 communicating with liquid output port 53, and a filtration member 58. A portion of the walls of one or both of the input and output shells 50, 52, respectively, may comprise, or be associated with, a thermoelectric cooling device or surface. The filtration member itself may alternatively, or additionally, comprise, or be associated with, a thermoelectric cooler.

In the exemplary filtration device shown in FIGS. 3A and 3B, a sample liquid/solids input shell 50 and a liquid output shell 52 have generally similar structures and configurations and have mating, interfacing surfaces that may be sealed to provide substantially sealed internal chambers. In the prototype embodiment shown, at least a portion of input shell 50 and/or output shell 52 comprise a thermoelectrically cooled surface 54 forming a shell wall. In an alternative embodiment, each of input shell 50 and output shell 52 are provided with a thermoelectrically cooled surface. The filtration element is mounted between the input and output shells when the filtration device is assembled and may be arranged in a substantially vertical orientation during use, as described previously.

Filtration element 58, shown in the prototype device as a mesh screen, is mounted between input and output shells 50 and 52 and serves to define the chambers. In the embodiment illustrated, filtration element 58 comprises a mesh screen constructed from a biocompatible, sterilizable material having a desired pore size. Filtration element 58 may be actively or passively cooled, and preferably comprises a material having a generally high temperature conductivity. In the embodiment illustrated in FIGS. 3A and 3B, filtration element 58 and the solids it traps are cooled by contact with and/or proximity to the thermoelectrically cooled surface(s) of the input and/or output chambers 50 and 52.

Figure 4:
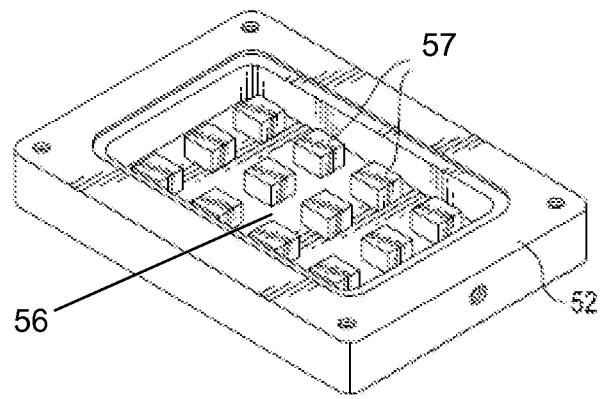
FIG. 4 illustrates a schematic diagram of a cooling chamber for another exemplary cooled filtration device of the present invention.

In another embodiment illustrated in FIG. 4, a filtration device may comprise a chamber surface 56 having posts 57 or other surface area enlargements, such as fins, ridges, or the like, that increase the cooling surface area provided in proximity to the filtration element and the liquid/solids input, the filtrate, and/or the liquid output. In one embodiment, posts 57 or other types of raised surfaces maybe provided in contact with the filtration element to transfer heat away from the filtration element, thereby increasing cooling of the filtration element and the filtrate associated with it.

While the cooled filtration device of the present invention has been described with reference to a thermoelectrically cooled prototype, it will be appreciated that other cooling mechanisms and systems may be incorporated in a filtration device of the present invention. Cooling of the filtered solids may be achieved, for example, by forced air convection on or across a filtration member, or by liquid cooling, directly or indirectly, of a filtration member or surface, by $H_2$Ceramic cooling, or using other cooling techniques and combinations of cooling techniques.

When thermoelectric cooling surfaces are employed in filtration devices of the present invention, the thermoelectric cooling device is preferably connected to a DC power source. In one embodiment, the filtration assembly comprises a housing enclosing a thermoelectric cooling device connectible to a DC power source, a thermoelectrically cooled filtration device with an optional insulation jacket mounted to (inside or outside of) the housing, and a heat sink or fan for dissipating heat generated by the thermoelectric cooling device.

FIG. 5 shows an alternative embodiment in which filtration assembly having a liquid/solids input conduit 60 feeding the liquid/solids input chamber defined by filtration shell member 62 and a liquid output conduit 64 for withdrawing liquid effluent from an output chamber defined by filtration shell member 66 is mounted in a cooling jacket 68. The cooling jacket 68 may contact and provide cooling to some of the surfaces of the filtration device, as illustrated in FIG. 5 or, in alternative embodiments, it may substantially surround and contact substantially the entire surface area of the filtration device to provide cooling to the device and its contents. When the filtration device is provided with integrated cooling mechanisms, as described above, and additional cooling is not required, an insulated jacket having a similar configuration may be provided to maintain the cooled temperatures of the filtration device and its contents.

Filtration devices of the present invention may be provided in many different configurations and orientations. In one embodiment, a cooled filtration device may be used with the filtration member in a standard, generally horizontal orientation with a liquid/solids collection chamber provided above the filtration element and a liquid withdrawal chamber provided below the filtration element. For filtration applications where clogging of the filter and consequent disruption of an interventional procedure are problematic, the cooled filtration device preferably incorporates a filtration element provided in a generally vertical orientation, as described above.

The filtration member may be an "installed feature" of the filtration device and the filtration device may be provided as a single-use, disposable assembly. Alternatively, filtration members may be provided as components that are removable from the filtration device to facilitate collection and further processing and analysis of solids. The filter may be removable upon disassembly or partial disassembly of the filtration device, as illustrated in the exemplary prototype shown in FIGS. 3A and 3B. In an alternative embodiment, the filtration member may be mountable in a carrier structure that is insertable into and removable from the filtration device, thereby facilitating removal and replacement of filtration elements during a filtration procedure. The filtration element carrier structure is preferably sealable in the filtration device so that desired vacuum and aspiration conditions are maintained during filtration, and may incorporate a tab or handle to facilitate positioning and withdrawing of the filtration element. Using such an insertable and removable carrier device, filtration members may be replaced or substituted during an interventional procedure without significant delays or disruptions in the procedure. The filtration element may be provided as a disposable and separately packaged element, while the filtration device, including the cooling mechanism, may be provided as a reusable device.

The filtration member and filtration device may be provided as an integrated unit that may be "plugged into" or mounted "in-line" with another sample collection or interventional device, or it may be provided as an integrated component with a sample collection or interventional device. FIG. 6A, for example, shows a highly schematic diagram illustrating a filtration system of the present invention integrated in an interventional aspirating atherectomy or thrombectomy device. In this system, an operating head 70 of an interventional catheter having a port for withdrawal of biological materials is guided to a target interventional site such as a blood vessel, and operated to remove biological materials from the target site. A liquid/solids mixture withdrawn from the site is conveyed through catheter 72, transits or bypasses an interventional catheter control mechanism 74, and is conveyed to a filtration device 76. Solid filtrate is separated from liquid components and collected during passage through the filtration device, and a substantially liquid effluent is discharged for disposal and/or collection in a liquid collection chamber. The solids may be removed from the filtration member and further processed or dispatched for analytical testing.

FIG. 6B shows an alternative arrangement of similar components, in which an operating head 70 of an interventional catheter having a port for withdrawal of biological materials is guided to a target interventional site such as a blood vessel, and operated to remove biological materials from the target site. A liquid/solids mixture withdrawn from the site is conveyed through catheter 72 to a filtration device 76. Solid filtrate is separated from liquid components and collected during passage through the filtration device, and a substantially liquid effluent is discharged and transits, or bypasses an interventional catheter control mechanism 74 for disposal and/or collection in a liquid collection chamber. The solids may be removed with the filtration member and further processed or dispatched for analytical testing.

Multiple filtration devices may be provided in series or in parallel with respect to sample collection and liquid removal devices. In one embodiment, for example, multiple filtration devices having filtration members with different pore sizes, may be provided. In general, downstream filtration devices have filtration members with smaller pore sizes than the upstream devices. A series of progressively smaller filtration members may be provided in a single filtration device of the present invention, or in multiple filtration devices arranged in series. In one embodiment, a filtration device of the present invention is mounted in-line between the outlet (low pressure side) of an aspiration pump and a collection bag. An unfiltered aspirate or sample bypass path may also be provided that avoids filtration and routes a portion of the liquid/solids mixture directly to an aspirate collection receptacle.

The liquid effluent separated from solids during filtration contains soluble biomarkers and components and may also be useful for testing and analysis. The liquid effluent may also be actively or passively cooled using methods and systems of the present invention, as described above.

Filtered solids and/or filtrate collected using filtration methods and systems of the present invention may be subjected to further processing or preserved for analytical testing. Many sample preparation techniques are known and may be used in sample processing. Samples collected during filtration using methods and systems of the present invention may be mechanically removed from the filtration element using a scraping device and collected in a sterile, sealable container, or the solids may be removed and collected using a liquid or gas stream. Washing of the filtration element and removal of the collected solids with cold, sterile water is preferred for many downstream analytical tests. The washed water/solids mixture may be centrifuged using a cooled centrifuge, and the solids frozen or resuspended and frozen for future analytical testing. In one embodiment, cooled solids are removed from the filtration member and washed in cold, sterile water, then frozen in liquid nitrogen. Samples may be transported for processing in a frozen state.

Many different types of analytical tests may be conducted on samples collected using methods and devices of the present invention. Gene expression activity may be detected and identified, for example, using Real-Time quantitative polymerase chain reaction (RT-qPCR) techniques to analyze the primary gene expression product, mRNA. Analysis of both targeted proteins and novel proteins may also be conducted using samples isolated in filtration devices of the present invention. Targeted protein analysis may be conducted using, for example, Western blotting and Luminex™ techniques.

Exemplary genes that are desirable to target, and assay for, in vascular disease are listed in Table 2, below.

EXAMPLES

Aspirate was collected during a rotational atherectomy procedure using an aspirating, rotational atherectomy device substantially as described in U.S. Pat. No. 6,818,001. The aspirate was filtered using a standard filtration device that did not incorporate a generally vertical filtration element or a cooling element, with pore sizes of 40 and 70 micron. The filtered solids were frozen in liquid nitrogen and transported to a research laboratory for analysis. After experiencing significant difficulties isolating mRNA and protein from several samples, both mRNA and protein were successfully isolated from two samples and analyzed. Although the samples underwent degradation consistent with a lack of cooling during sample collection, the results presented below demonstrate that plaque samples collected during rotational atherectomy procedures provide adequate protein and mRNA isolation and integrity for analysis, and that RT-PCR and 2D protein analysis may be performed on such samples. Samples collected using a cooled filtration device as disclosed herein are expected to provided improved protein and mRNA integrity.

mRNA Integrity

1. Spectrophotometric Analysis

Spectrophotometric analyses for two biological samples collected during a rotational atherectomy procedure were performed. The spectrophotometric analyses for these 2 samples were typical of that for other types of mRNA samples. The purity of the sample was demonstrated by the 260/280 ratio of 2.0±0.1. The total quantity of mRNA isolated was measured at between 1.5 and 3 micrograms. Expression analyses can be performed on as little as 0.5 micrograms of mRNA using Real Time Quantitative PCR (RT-PCR).

2. Denaturing Gel Analysis

The above biological samples were analyzed for RNA integrity. The RNA was denatured and separated into its components using gel electrophoresis. The larger particles travel slower and the smaller particles travel faster. Ribosomal RNA is the most abundant RNA form and migrates as two distinct sizes with the 28 s being 5.0 kilobases (kb) in length and the 18 s being 1.9 kb. The samples collected as described above showed two distinct RNA bands. There was evidence of RNA degradation in these samples, which was attributed to sample handling and delays in cooling the samples. This was evidenced by a reduction in the intensity of the upper band. Degradation at this level is generally not of significant consequence for a preliminary RT-PCR analysis, but improved sample integrity provides improved resolution and results.

Protein Analysis

Specific proteins of interest in biological samples may be isolated and analyzed. For example, the level of various proteins, including C-reactive protein and other inflammatory cytokines, may be elevated or modulated during disease. Proteins that may be assayed using analytical techniques of the present invention are listed in Table 2, below. Thus, according to methods of the present invention, biological samples withdrawn from a target site may be filtered, as described above, and analyzed to determine the presence (or absence) and the prevalence, distribution and/or concentration of proteins listed in Table 2.

Proteins may be isolated from the plaque and analytical methods employed to identify differences in specific proteins, for example using antibodies that are specific for the protein of interest. A more robust signal identifies a greater amount of the specific protein of interest. This can be performed for one protein at a time using methods such as Western blotting, or multiple proteins may be assayed simultaneously using techniques such as the Luminex™ technology (Luminex Corp., Austin, Tex.). Simple protein analysis techniques were used with the patient samples described above.

1. Coomasie Stain

Protein isolation resulted in approximately 1000-2000 micrograms of protein from each of the samples. The sample with the larger protein quantity (collected and analyzed for RNA, above) was placed on a gel for protein separation by means of electrophoresis, and the gel was stained with a blue dye. A control gel included molecular weight markers (a standard to measure protein size in kilodaltons (kD)). Proteins of various molecular weights were isolated and were visible on the sample gels.

2. Western Blot

The protein in the gel was transferred out of the gel matrix and onto a surface, or membrane. Proteins can be identified by probing this surface with antibodies specific for a protein in question and are found as a narrow band at a specific molecular weight. Protein degradation interferes with this identification process or broadens the band that is identified. The molecular weight marker does not show up when the transferred proteins are probed with the antibody. The protein in the sample described above having the most dense band was probed for beta-actin (a 45 kD protein), with the results demonstrating narrow bands at approximately 45 kD in size corresponding to the band noted on the stained gels.

3. Novel Protein Expression

Novel proteins and biomarkers that are involved in beneficial or detrimental adaptations in vascular plaque (and other disease conditions) may also be identified. The proteins may be separated using a multistep process (e.g., two-dimensional gel electrophoresis). The proteins of interest are subsequently identified using mass spectroscopy. This is particularly important for new drug development. Another tissue sample was collected and the proteins were separated as described above. Two gels were run, one stained in blue and the other in orange, for biological samples obtained as described above. Novel proteins were identified as those with spots of an individual color without closely overlying spots of the different color. Several novel proteins were apparent from the gels.

Table 2, below, lists exemplary genes that may be present in biological materials removed from blood vessels and may be assayed for the presence of vascular disease. The exemplary genes and proteins expressed by those genes may also be assayed using methods and systems of the present invention to monitor the progress and efficacy of treatment protocols.

TABLE 2

Exemplary Genes to assay for Vascular Disease

| Symbol | Description | Gene Name |
|---|---|---|
| ABCA1 | ATP-binding cassette, sub-family A (ABC1), member 1 | ABC-1/ABC1 |
| ACE | Angiotensin I converting enzyme (peptidyl-dipeptidase A) 1 | ACE1/CD143 |
| ADFP | Adipose differentiation-related protein | ADRP |
| APOA1 | Apolipoprotein A-I | MGC117399 |
| APOB | Apolipoprotein B (including Ag(x) antigen) | FLDB |
| APOE | Apolipoprotein E | AD2/apoprotein |
| BAX | BCL2-associated X protein | Bax zeta |
| BCL2 | B-cell CLL/lymphoma 2 | Bcl-2 |
| BCL2A1 | BCL2-related protein A1 | BCL2L5/BFL1 |
| BCL2L1 | BCL2-like 1 | BCL-XL/S |
| BID | BH3 interacting domain death agonist | MGC15319 |
| BIRC3 | Baculoviral IAP repeat-containing 3 | AIP1/API2 |
| CCL2 | Chemokine (C-C motif) ligand 2 | GDCF-2/GDCF-2 HC11 |
| CCL5 | Chemokine (C-C motif) ligand 5 | D17S136E/RANTES |
| CCR1 | Chemokine (C-C motif) receptor 1 | CKR-1/CMKBR1 |
| CCR2 | Chemokine (C-C motif) receptor 2 | CC-CKR-2/CCR2A |
| CD44 | CD44 antigen (Indian blood group) | CDW44/ECMR-III |
| CDH5 | Cadherin 5, type 2, VE-cadherin (vascular epithelium) | 7B4 |
| CFLAR | CASP8 and FADD-like apoptosis regulator | CASH/CASP8AP1 |
| COL3A1 | Collagen, type III, alpha 1 (Ehlers-Danlos syndrome type IV, autosomal dominant) | EDS4A |
| CSF1 | Colony stimulating factor 1 (macrophage) | MCSF |

TABLE 2-continued

Exemplary Genes to assay for Vascular Disease

| Symbol | Description | Gene Name |
| --- | --- | --- |
| CSF2 | Colony stimulating factor 2 (granulocyte-macrophage) | GMCSF |
| CTGF | Connective tissue growth factor | CCN2/IGFBP8 |
| EGR1 | Early growth response 1 | AT225/G0S30 |
| ELN | Elastin (supravalvular aortic stenosis, Williams-Beuren syndrome) | SVAS/WBS |
| ENG | Endoglin (Osler-Rendu-Weber syndrome 1) | CD105/END |
| FABP3 | Fatty acid binding protein 3, muscle and heart (mammary-derived growth inhibitor) | FABP11/H-FABP |
| FAS | Fas (TNF receptor superfamily, member 6) | ALPS1A/APO-1 |
| FGA | Fibrinogen alpha chain | Fib2 |
| FGF2 | Fibroblast growth factor 2 (basic) | BFGF/FGFB |
| FN1 | Fibronectin 1 | CIG/DKFZp686F10164 |
| HBEGF | Heparin-binding EGF-like growth factor | DTR/DTS |
| ICAM1 | Intercellular adhesion molecule 1 (CD54), human rhinovirus receptor | BB2/CD54 |
| IFNAR2 | Interferon (alpha, beta and omega) receptor 2 | IFN-R/IFN-alpha-REC |
| IFNG | Interferon, gamma | IFG/IFI |
| IL1A | Interleukin 1, alpha | IL-1A/IL1 |
| IL1R1 | Interleukin 1 receptor, type I | CD121A/D2S1473 |
| IL1R2 | Interleukin 1 receptor, type II | IL1RB |
| IL2 | Interleukin 2 | IL-2/TCGF |
| IL3 | Interleukin 3 (colony-stimulating factor, multiple) | IL-3/MCGF |
| IL4 | Interleukin 4 | BSF1/IL-4 |
| IL5 | Interleukin 5 (colony-stimulating factor, eosinophil) | EDF/IL-5 |
| ITGA2 | Integrin, alpha 2 (CD49B, alpha 2 subunit of VLA-2 receptor) | BR/CD49B |
| ITGA5 | Integrin, alpha 5 (fibronectin receptor, alpha polypeptide) | CD49e/FNRA |
| ITGAX | Integrin, alpha X (antigen CD11C (p150), alpha polypeptide) | CD11C |
| ITGB2 | Integrin, beta 2 (antigen CD18 (p95), lymphocyte function-associated antigen 1; macrophage antigen 1 (mac-1) beta subunit) | CD18/LAD |
| KDR | Kinase insert domain receptor (a type III receptor tyrosine kinase) | FLK1/VEGFR |
| KLF2 | Kruppel-like factor 2 (lung) | LKLF |
| LAMA1 | Laminin, alpha 1 | LAMA |
| LDLR | Low density lipoprotein receptor (familial hypercholesterolemia) | FH/FHC |
| LIF | Leukemia inhibitory factor (cholinergic differentiation factor) | CDF/D-FACTOR |
| LPA | Lipoprotein, Lp(a) | AK38/APOA |
| LPL | Lipoprotein lipase | LIPD |
| MMP1 | Matrix metallopeptidase 1 (interstitial collagenase) | CLG/CLGN |
| MMP3 | Matrix metallopeptidase 3 (stromelysin 1, progelatinase) | SL-1/STMY |
| MSR1 | Macrophage scavenger receptor 1 | CD204/SCARA1 |
| NFKB1 | Nuclear factor of kappa light polypeptide gene enhancer in B-cells 1 (p105) | DKFZp686C01211/EBP-1 |
| NOS3 | Nitric oxide synthase 3 (endothelial cell) | ECNOS/NOS III |
| NPY | Neuropeptide Y | PYY4 |
| NR1H3 | Nuclear receptor subfamily 1, group H, member 3 | LXR-a/LXRA |
| PDGFA | Platelet-derived growth factor alpha polypeptide | PDGF-A/PDGF1 |
| PDGFB | Platelet-derived growth factor beta polypeptide (simian sarcoma viral (v-sis) oncogene homolog) | PDGF2/SIS |
| PDGFRB | Platelet-derived growth factor receptor, beta polypeptide | CD140B/JTK12 |
| PPARA | Peroxisome proliferative activated receptor, alpha | NR1C1/PPAR |
| PPARD | Peroxisome proliferative activated receptor, delta | FAAR/NR1C2 |
| PPARG | Peroxisome proliferative activated receptor, gamma | HUMPPARG/NR1C3 |
| PTGS1 | Prostaglandin-endoperoxide synthase 1 (prostaglandin G/H synthase and cyclooxygenase) | COX1/COX3 |
| RXRA | Retinoid X receptor, alpha | NR2B1 |
| SELE | Selectin E (endothelial adhesion molecule 1) | CD62E/ELAM |
| SELL | Selectin L (lymphocyte adhesion molecule 1) | CD62L/LAM-1 |
| SELPLG | Selectin P ligand | CD162/PSGL-1 |
| SERPINB2 | Serpin peptidase inhibitor, clade B (ovalbumin), member 2 | HsT1201/PAI |
| SERPINE1 | Serpin peptidase inhibitor, clade E (nexin, plasminogen activator inhibitor type 1), member 1 | PAI/PAI-1 |
| SOD1 | Superoxide dismutase 1, soluble (amyotrophic lateral sclerosis 1 (adult)) | ALS/ALS1 |
| SPP1 | Secreted phosphoprotein 1 (osteopontin, bone sialoprotein I, early T-lymphocyte activation 1) | BNSP/BSPI |
| TGFB1 | Transforming growth factor, beta 1 (Camurati-Engelmann disease) | CED/DPD1 |
| TGFB2 | Transforming growth factor, beta 2 | TGF-beta2 |
| THBS4 | Thrombospondin 4 | TSP4 |
| TNC | Tenascin C (hexabrachion) | HXB/TN |
| TNF | Tumor necrosis factor (TNF superfamily, member 2) | DIF/TNF-alpha |
| TNFAIP3 | Tumor necrosis factor, alpha-induced protein 3 | A20/TNFA1P2 |
| VCAM1 | Vascular cell adhesion molecule 1 | DKFZp779G2333/INCAM-100 |
| VEGF | Vascular endothelial growth factor | VEGFA/VPF |
| VWF | Von Willebrand factor | F8VWT/VWD |
| 18SrRNA | Human 18S ribosomal RNA | 18SRNA |
| HPRT1 | Hypoxanthine phosphoribosyltransferase 1 (Lesch-Nyhan syndrome) | HGPRT/HPRT |
| RPL13A | Ribosomal protein L13a | RPL13A |
| GAPDH | Glyceraldehyde-3-phosphate dehydrogenase | G3PD/GAPD |
| ACTB | Actin, beta | b-Actin |

The present invention has been described with reference to specific device embodiments and figures. These specific embodiments should not be construed as limitations on the scope of the invention, but merely as illustrations of exemplary embodiments. It is further understood that many modifications, additions and substitutions may be made to the described interventional catheter and control system without departing from the scope of the present invention.

I claim:

1. A cooled filtration assembly for filtering biological materials comprising a housing having a liquid/solids input chamber and a liquid output chamber; a liquid/solids input port communicating with the liquid/solids input chamber, a liquid output port communicating with the liquid output chamber, and a filtration member interposed between the liquid/solids input chamber and the liquid output chamber, wherein the filtration member comprises a thermoelectric cooling surface that is actively cooled during operation and filtrate comprising biological materials residing in the filtration assembly during a filtration operation is cooled to a temperature at least 20° F. cooler than the temperature of biological materials entering the liquid/solids input port.

2. The cooled filtration assembly of claim 1, wherein the filtration member is oriented in a generally vertical orientation during operation of the cooled filtration assembly.

3. The cooled filtration assembly of claim 1, additionally comprising a jacket mountable on the filtration assembly and comprising an active or passive cooling system.

4. The cooled filtration assembly of claim 1, additionally comprising an insulating jacket mountable on the filtration assembly.

5. The cooled filtration assembly of claim 1, wherein the filtration member comprises a size exclusion filtration member.

6. The cooled filtration assembly of claim 1, wherein the cooled filtration assembly comprises an additional port in proximity to the liquid/solids input chamber for introduction of a cooled fluid during the filtration operation.

7. The cooled filtration assembly of claim 1, wherein at least one of the liquid/solids input chamber and the liquid output chamber additionally incorporates an active cooling element.

8. A cooled filtration assembly for filtering biological materials comprising a liquid/solids input port communicating with a liquid/solids input chamber, a liquid output chamber and a liquid output port communicating with the liquid output chamber, and a filtration member interposed between the liquid/solids input chamber and the liquid output chamber, wherein at least one of the liquid/solids input chamber, the liquid output chamber and the filtration member is actively cooled during operation and filtrate comprising biological materials residing in the filtration assembly during a filtration operation is cooled to a temperature at least 20° F. cooler than the temperature of biological materials entering the liquid/solids input port, wherein the filtration member is oriented in a generally vertical orientation during operation of the cooled filtration assembly and extends less than the full height of the liquid/solids input chamber and liquid output chamber, leaving a gap permitting material to flow between the liquid/solids input chamber and the liquid output chamber.

9. The cooled filtration assembly of claim 8, wherein at least one of the liquid/solids input chamber, the liquid output chamber and the filtration member comprises a thermoelectric cooling surface.

10. The cooled filtration assembly of claim 8, additionally comprising a jacket mountable on the filtration assembly and comprising an active or passive cooling system.

11. The cooled filtration assembly of claim 8, additionally comprising an insulating jacket mountable on the filtration assembly.

12. The cooled filtration assembly of claim 8, wherein the filtration member comprises a size exclusion filtration member.

13. The cooled filtration assembly of claim 8, wherein the cooled filtration assembly comprises an additional port in proximity to the liquid/solids input chamber for introduction of a cooled fluid during a filtration operation.

14. An aspirating system for withdrawal of biological materials from a subject comprising a distal operating head for withdrawing a biological liquid/solids mixture sample from a target interventional site in the subject, a catheter having a lumen for transporting the biological liquid/solids mixture sample in a proximal direction, and a cooled filtration assembly comprising a liquid/solids input port communicating with a liquid/solids input chamber, a liquid output chamber and a liquid output port communicating with the liquid output chamber, and a filtration member interposed between the liquid/solids input chamber and the liquid output chamber, wherein the filtration member comprises a thermoelectric cooling surface, whereby the filtration member is actively cooled during operation and filtrate comprising biological materials residing in the filtration assembly during a filtration operation is cooled to a temperature at least 20° F. cooler than the temperature of biological materials entering the liquid/solids input port.

15. An aspirating system of claim 14, additionally comprising a reservoir for collecting the biological liquid/solids mixture sample prior to passage of the biological liquid/solids mixture sample to the cooled filtration assembly.

16. A filtration device for filtering biological materials comprising a liquid/solids input port communicating with a liquid/solids input chamber, a liquid output chamber and a liquid output port communicating with the liquid output chamber, and a filtration member interposed between the liquid/solids input chamber and the liquid output chamber, wherein at least one of the liquid/solids input chamber, the liquid output chamber and the filtration member is actively cooled during operation and the filtration member is adapted to be oriented in a substantially vertical orientation during a filtration operation, wherein the filtration member extends less than the full height of the liquid/solids input chamber and liquid output chamber, leaving a gap permitting material to flow between the iquid/solids input chamber and the liquid output chamber.

17. A method for processing a biological sample comprising:
  (a) withdrawing a liquid/solids mixture comprising a target tissue sample from a target site in a subject;
  (b) conveying the liquid/solids mixture to a filtration device comprising a liquid/solids input port communicating with a liquid/solids input chamber, a liquid output chamber and a liquid output port communicating with the liquid output chamber, and a filtration member interposed between the liquid/solids input chamber and the liquid output chamber, wherein at least one of the liquid/solids input chamber, the liquid output chamber and the filtration member is actively cooled during operation for separation of at least a fraction of the solids from liquids, and wherein the filtration member extends less than the full height of the liquid/solids input chamber and the liquid output chamber, leaving a gap permitting material to flow between the input and output chambers and is adapted to be oriented in a substantially vertical orientation during a filtration operation, whereby the solids reside in the filtration device and the liquids are withdrawn from the filtration device;
  (c) actively cooling the solids residing in the filtration device to produce cooled solids; and
  (d) analyzing the cooled solids.

18. A method of claim 17, wherein the target tissue sample comprises solids removed from blood vessels.

19. A method of claim 17, additionally comprising removing the cooled solids from the filtration device and washing them with cold, sterile water to provide washed solids; pelleting and freezing the washed solids.

20. A method of claim 17, additionally comprising assaying the cooled solids for expression of at least one gene encoding a protein selected from the group consisting of: ATP-binding cassette, sub-family A (ABC1), member 1: Angiotesin I converting enzyme (peptidyl-dipeptidase A) 1; Adipose differentiation-related protein; Apolipoprotein A-I; Apolipoprotein B (including Ag(x) antigen); Apolipoprotein E; BCL2-associated X protein; B-cell CLL/lymphoma 2; BCL2-related protein A1; BCL2-like 1; BH3 interacting domain death agonist; Baculoviral IAP repeat-containing 3;

Chemokine (C-C motif) ligand 2; Chemokine (C-C motif) ligand 5; Chemokine (C-C motif) receptor 1; Chemokine (C-C motif receptor 2; CD44 antigen (Indian blood group); Cadherin 5, type 2, VE-cadherin (vascular epithelium); CASP8 and FADD-like apoptosis regulator; Collagen, type III, alpha I (Ehlers-Danlos syndrome type IV, autosomal dominant); Colony stimulating factor 1 (macrophage); Colony stimulating factor 2 (granulocyte-macrophage); Connective tissue growth factor; Early growth response 1; Elastin (supravalvular aortic stenosis, Williams-Beuren syndrome); Endoglin (Osler-Rendu-Weber syndrome 1); Fatty acid binding protein 3, muscle and heart (mammary-derived growth inhibitor); Fas (TNF receptor superfamily, member 6); Fibrinogen alpha chain; Fibroblast growth factor 2 (basic); Fibronectin 1; Heparin-binding EGF-like growth factor; Intercellular adhesion molecule 1 (CD54), human rhinovirus receptor; Interferon (alpha, beta and omega) receptor 2; Interferon, gamma; Interleukin 1, alpha; Interleukin 1 receptor, type I; Interleukin 1 receptor, type II; Interleukin 2; Interleukin 3 (colony-stimulating factor multiple); Interleukin 3; Interleukin 5 (colony-stimulating factor, eosinphil); Intergrin, alpha 2 (CD49B), alpha 2 subunit of VLA-2 receptor); Intergin, alpha 5 (fibronectin receptor, alpha polypeptide); Intergrin, alpha X (antigen CD11C (p150), alpha polypeptide); Intergrin, beta 2 (antigen CD18 (p95), lymphocyte function-associated antigen 1; macrophage antigen 1 (mac-1) beta subunit); Kinase insert domain receptor (a type III receptor tyrosine kinase); Kruppel-like receptor 2 (lung); Laminin, alpha 1; Low density lipoprotein receptor (familial hypercholesterolemia); Leukemia inhibitory factor (cholinergic differentiation factor); Lipoprotein, Lp(a); Lipoprotein lipase; Matrix metallipeptidase 1 (interstitial collagenase); Matrix metallopeptidase 3 (stromelysin 1, progelatinase); Macrophage scavenger receptor 1; Nuclear factor of kappa light polypeptide gene enhancer in B-cells 1 (p105); Nitric oxide synthase 3 (endothelial cell); Neuropeptide Y; Nuclear receptor subfamily 1, group H, member 3; Platelet-derived growth factor alpha polypeptide; Platelet-derived growth factor beta polypeptide (simian sarcoma viral (v-sis) oncogene homolog); Platelet-derived growth factor receptor, beta polypeptide; Peroxisome proliferative activated receptor, alpha; Peroxisome proliferative activated receptor, delta; Peroxisome proliferative activated receptor, gamma; Prostaglandin-endoperoxide synthase 1 (prostaglandin G/H synthase and cyclooxygenase); Retinoid X receptor, alpha; Selectin E (endothelial adhesion molecule 1); Selectin L (lymphocyte adhesion molecule 1); Selectin P ligand; Serpin peptidase inhibitor, clade B (ovalbumin), member 2; Serpin peptidase inhibitor, clade E (nexin, plasminogen activator inhibitor type I), member 1; Superoxide dismutase 1, soluble (amyotrophic lateral sclerosis 1 (adult)); Secreted phosphoprotein 1 (osteopontin, bone sialoprotein I, early T-lymphocyte activation 1); Transforming growth factor, beta 1 (Camurati-Engelmann disease); Transforming growth factor, beta 2; Thrombospondin 4; Tenasein C (hexabrachion); Tumor necrosis factor (TNF superfamily, member 2); Tumor necrosis factor, alpha-induced protein 3; Vascular cell adhesion molecule 1; Vascular endothelial growth factor; Von Willebrand factor; Human 18S ribosomal RNA; Hypoxanthine phosphoribosyltransferase 1 (Lesch-Nyhan syndrome); Ribosomal protein L13a; Glyceraldehyde-3-phosphate dehyrogenase; and Actin, beta.

21. A tissue sampling assembly for withdrawal of biological materials from a subject comprising a sample removal device for removing a biological sample and a cooled filtration assembly comprising a liquid/solids input port communicating with a liquid/solids input chamber, a liquid output chamber and a liquid output port communicating with the liquid output chamber, and a filtration member interposed between the liquid/solids input chamber and the liquid output chamber, wherein the filtration member comprises a thermoelectric cooling surface, whereby the filtration member is actively cooled during operation and filtrate comprising biological materials residing in the filtration assembly during a filtration operating is cooled to a temperature at least 20° F. cooler than the temperature of biological materials entering the liquid/solids input port.

\* \* \* \* \*

UNITED STATES PATENT AND TRADEMARK OFFICE
CERTIFICATE OF CORRECTION

PATENT NO.         : 8,784,654 B2
APPLICATION NO.    : 12/742908
DATED              : July 22, 2014
INVENTOR(S)        : Wulfman It is certified that error appears in the above-identified patent and that said Letters Patent is hereby corrected as shown below:

In the Specification

Columns 3 & 4, in Table 1, under "Marker"
Line 4: delete "(sICAM-1)" and insert therefor -- (SICAM-1) --.

Columns 5 & 6, in Table 1, under "Laboratory Method"
Line 5: delete "cantitative enzyme" and insert therefor -- quantitative enzyme --.

Column 13
Line 58: delete "Coomasie" and insert therefor -- Coomassie --.

In the Claims

Column 18
Line 8: in Claim 15, delete "An aspirating" and insert therefor -- The aspirating --.
Line 25: in Claim 16, delete "iquid/solids" and insert therefor -- liquid/solids --.
Line 52: in Claim 18, delete "A method" and insert therefor -- The method --.
Line 54: in Claim 19, delete "A method" and insert therefor -- The method --.
Line 58: in Claim 20, delete "A method" and insert therefor -- The method --.
Lines 61-62: in Claim 20, delete "member 1: Angiotesin" and insert therefor -- member 1; Angiotensin --.

Column 19
Line 3: in Claim 20, delete "(C-C motif" and insert therefor -- (C-C motif) --.
Line 6: in Claim 20, delete "alpha I" and insert therefor -- alpha 1 --.
Line 20: Claim 20, delete "factor multiple); Interleukin 3;" and insert therefor -- factor, multiple); Interleukin 4; --.
Line 21: in Claim 20, delete "eosinphil); Intergin," and insert therefor -- eosinophil); Integrin, --.

Signed and Sealed this
Second Day of December, 2014

Michelle K. Lee
*Deputy Director of the United States Patent and Trademark Office*

Column 19
Lines 22-23: in Claim 20, delete "Intergin," and insert therefor -- Integrin, --.
Lines 23-24: in Claim 20, delete "Intergin, alpha X" and insert therefor -- Integrin, alpha X --.
Line 25: in Claim 20, delete "Intergrin, beta 2" and insert therefor -- Integrin, beta 2 --.
Line 28: in Claim 20, delete "receptor 2" and insert therefor -- factor 2 --.
Line 32: in Claim 20, delete "metallipeptidase" and insert therefor -- metallopeptidase --.

Column 20
Lines 10-11: in Claim 20, delete "type I)," and insert therefor -- type 1), --.
Line 16: in Claim 20, delete "Tenasein" and insert therefor -- Tenascin --.
Line 22: in Claim 20, delete "dehyrogenase;" and insert therefor -- dehydrogenase; --.